US005886012A

United States Patent [19]
Pang et al.

[11] Patent Number: 5,886,012
[45] Date of Patent: Mar. 23, 1999

[54] METHOD OF TREATMENT FOR DISEASE ASSOCIATED WITH EXCESSIVE PHF USING COMBINATION THERAPY INVOLVING EXOGENOUS CALCIUM AND CALCIUM CHANNEL BLOCKERS

[75] Inventors: Peter K. T. Pang, 52225 Range Rd. 232, 205 Carriage Ln., Sherwood Park, Alberta, Canada, T8A 2A6; Richard Z. Lewanczuk, Edmonton, Canada; Christine G. Benishin, Ardrossan, Canada; Jie Shan, Edmonton, Canada

[73] Assignee: Peter K. T. Pang, Alberta, Canada

[21] Appl. No.: 833,779

[22] Filed: Apr. 9, 1997

Related U.S. Application Data

[63] Continuation of Ser. No. 540,396, Oct. 6, 1995, abandoned, which is a continuation-in-part of Ser. No. 264,078, Jun. 22, 1994, Pat. No. 5,457,132, which is a division of Ser. No. 997,329, Dec. 28, 1992, Pat. No. 5,350,771, which is a continuation of Ser. No. 750,590, Aug. 27, 1991, abandoned, which is a continuation-in-part of Ser. No. 460,482, Jan. 3, 1990, abandoned, which is a continuation-in-part of Ser. No. 327,450, Mar. 22, 1989, abandoned, said Ser. No. 264,078, is a continuation-in-part of Ser. No. 918,775, Jul. 27, 1992, Pat. No. 5,354,765, which is a continuation of Ser. No. 460,482, Jan. 3, 1990, abandoned, which is a continuation-in-part of Ser. No. 327,450, Mar. 22, 1989, abandoned.

[51] Int. Cl.$^6$ .................................................. A61K 31/44
[52] U.S. Cl. .......................... 514/356; 514/354; 514/355
[58] Field of Search .................................. 514/354, 355, 514/356

[56] References Cited

U.S. PATENT DOCUMENTS

| | | | |
|---|---|---|---|
| 3,975,539 | 8/1976 | Köppe et al. ............................ | 424/304 |
| 4,402,872 | 9/1983 | Bohn ....................................... | 260/112 |
| 4,443,549 | 4/1984 | Sadowski ................................ | 436/548 |
| 4,621,093 | 11/1986 | Ulrich et al. ............................ | 514/355 |
| 4,703,038 | 10/1987 | Garthoff et al. ........................... | 514/19 |
| 4,837,171 | 6/1989 | Codington .............................. | 436/548 |
| 4,855,300 | 8/1989 | Nandi et al. ............................ | 514/264 |
| 4,859,665 | 8/1989 | Garthoff et al. ........................ | 514/221 |
| 4,906,647 | 3/1990 | Kouchiwa et al. ...................... | 514/356 |
| 5,047,235 | 9/1991 | Lossnitzer et al. ....................... | 424/80 |

FOREIGN PATENT DOCUMENTS

| | | |
|---|---|---|
| 0 204 129 A2 | 12/1986 | European Pat. Off. . |
| 0 204 951 A2 | 12/1986 | European Pat. Off. . |
| 0 204 951 A3 | 12/1986 | European Pat. Off. . |
| 0 315 414 A1 | 5/1989 | European Pat. Off. . |
| 1154810 | 4/1961 | Germany . |
| 89/03836 | 10/1988 | WIPO . |

OTHER PUBLICATIONS

Federation Proceedings For Experimental Biology, vol. 45, No. 12, Nov. 12, 1986, Bethesda, MD; pp. 2739–2745, Lawrence M. Resnick et al., "Calcium Metabolism In Essential Hypertension: Relationship To Altered Renin System Activity."

Database WPI, Section Ch, Week 8809, Derwent Publications Ltd., London, GB; Class A96, AN 88–059842, XP002001479, & JP–A–63 014 715 (Zeria Shinyaku Kogy), Jan. 21, 1988.

Federation Proceedings For Experimental Biology, vol. 45, No. 12, Nov. 12, 1986, Bethesda, MD; pp. 2739–2745, Lawrence M. Resnick et al., "Calcium Metabolism In Essential Hypertension: Relationship To Altered Renin System Activity."

Bukoski et al., Biochem. and Biophys. Res. Comm., "Effect of 1.25 (OH)$_2$ Vitamin D$_3$ and Ionized Ca$^{2+}$ on $^{45}$Ca Uptake by Primary Cultures of Aortic Myocytes of Spontaneously Hypertensive and Wistar Kyoto Normotensive Rats", vol. 146, No. 3, pp. 1330–1335, 1987.

Park et al., American Physiological Society, "Calcium in the Control of Renin Release", pp. F22–F25, 1978.

Inoue et al., Biochem. and Biophys. Res. Comm., "1,25–Dihydroxyvitamin D$_3$ Stimulated $^{45}$Ca$^{2+}$–Uptake by Cultured Vascular Smooth Muscle Cells Derived from Rat Aorta", vol. 152, No. 3, pp. 1388–1394, 1988.

Baran et al., The Journal of Clin. Inves., "1,25 Dihydroxyvitamin D Increases Hepatocyte Cytosolic Calcium Levels", vol. 77, No. 5, 1986.

Resnick et al., Federation Proc., "Calcium Metabolism in Essential Hypertension: Relationship to Altered Renin System Activity", vol. 45, No. 12, 1986.

Matsumura et al., The Journnal of Pharm., "Inhibitory Effects of Calcium Channel Agonists on Renin Release from Rat Kidney Cortical Slices", vol. 241, No. 3, 1987.

Kotchen et al., The American Journal of Cardiology, "Effects of Calcium on Renin and Aldosterone", vol. 62, pp. 41G–46G, 1988.

Park et al., American Journal of Physiology, "Calcium in the Control of Renin Secretion: Ca$^{2+}$Influx as an Inhibitory Siganl", vol. 240pp. F70–F74, Index Only. (1981).

Glick et al., Anal. Chem., "Development of a Solid–Substrate Room–Temperature Luminescence Immunoassay", vol. 60, No. 18, pp. 1982–1984, 1988.

Reichstein et al., Anal. Chem., "Laser–Excited Time–Resolved Solid–Phase Fluoroimmunoassays with the New Europium Chelate 4, 7–Bis–(chloro–sulfophenyl)–1, 10–phenanthroline–2,9–dicarboxylic Acid as Label", vol. 60, No. 10, pp. 1069–1074, 1988.

Chem. Abstracts, vol. 109, p. 148, 1988.

Pharmacology, vol. 110, p. 43, 1989.

Fleckenstein et al., Zeitschrift für Kreislaufforschung, "Zum Wirkungsmechanismus neuartiger Koronardilatatoren mit gleichzeitig Sauerstoff–einsparenden Myokare–Effekten, Prenylamin und Iproverstril", vol. 56, No. 7, pp. 716–745,. (1980).

Dixon et al., Enzymes, Third Edit., pp. 35–37, 1979.

Hermsmeyer et al., Annals New York Acad. of Sci., "Calcium Channel Modulation by Dihydropyridines in Vascular Smooth Muscle", pp. 24–31. (1980).

Fleckenstein, Annals New York Acad. of Sci., "The Calcium Channel of the Heart", pp. 1–15.

Primary Examiner—Theodore J. Criares
Attorney, Agent, or Firm—Nikaido, Marmelstein, Murray & Oram LLP

[57] ABSTRACT

Hypotensive mammals are treated to lower mean blood pressure by administering synergistic amounts of a calcium blocking agent together with a calcium supplement.

3 Claims, 2 Drawing Sheets

METHOD OF TREATMENT FOR DISEASE ASSOCIATED WITH EXCESSIVE PHF USING COMBINATION THERAPY INVOLVING EXOGENOUS CALCIUM AND CALCIUM CHANNEL BLOCKERS

This is a continuation of application Ser. No. 08/540,396, filed Oct. 6, 1995, now abandoned, which is a continuation-in-part application of application Ser. No. 08/264,078, filed Jun. 22, 1994, now U.S. Pat. No. 5,457,132, which is a divisional of application Ser. No. 07/997,629, now U.S. Pat. No. 5,350,771, filed Dec. 28, 1992, which is a continuation of application Ser. No. 07/750,590, filed Aug. 27, 1991 (now abandoned), which is a continuation-in-part divisional application of Ser. No. 07/460,482, filed Jan. 3, 1990 (now abandoned), which is a continuation-in-part of application Ser. No. 07/327,450, filed Mar. 22, 1989 (now abandoned); application Ser. No. 08/264,078 is a continuation-in-part divisional application of application Ser. No. 07/918,775, now U.S. Pat. No. 5,354,765, filed Jul. 27, 1992, which is a continuation application of application Ser. No. 07/460,482, filed Jan. 3, 1990 (now abandoned), which is a continuation-in-part application of application Ser. No. 07/327,450, filed Mar. 22, 1989 (now abandoned).

BACKGROUND OF THE INVENTION

Calcium channel blockers were identified as a method for the control of hypertension, as reported by Fleckenstein et al., *Z. Kreislaufforsch*, 56, 716 (1967), and are routinely used in the control of hypertension. Three calcium channel blockers are currently of clinical significance in the United States, verapamil, nifedipine and diltiazem. All three achieve their anti-hypertensive effect by inhibiting the entry of calcium ions into vascular smooth muscle. The ultimate effect is vasodilation.

Hypertensive hormones, such as the renin-angiotensin system (RAS), the vitamin D system, and the parathyroid hypertensive factor (PHF), are all causative factors in stimulating the increase of calcium ions in vascular smooth muscle. PHF is disclosed and described in patent application Ser. No. 07/327,450.

It has been found that calcium supplements, in dietary form, may inhibit the RAS, PHF and vitamin D systems, [Park et al., *Am. J. Physiol.*, 235, F22 (1978); Park et al., *Am. J. Physiol.*, 240, F70 (1981); Hotchen et al., *Am. J. Cardiol.*, 62, 41G (1988); Bukoski et al., *B.B.R.C.*, 147, 1330 (1987); Inoue et al., *B.B.R.C.*, 152, 1388 (1988); Baran et al., *J. Clin. Invest.*, 77, 1622 (1986); Lewanczuk et al., *Am. J. Hypertens.*, 3:349 (1990)] and are, therefore, beneficial in decreasing calcium uptake in vascular smooth muscle. An untoward effect of calcium supplementation is that the increased bio-availability of calcium partially negates the inhibitory effect on the endocrine system. Calcium channel blockers, by limiting the uptake of calcium in vascular smooth muscle, are beneficial, but have been found to stimulate some endocrine systems, such as the RAS system. (Kotchen et al., *Am. J. Cardiol.*, 62 41G (1988); Matsumara et al., *J. Pharmacol. Exp. Ther.*, 241, 1000 (1978); Resnick et al., *Fed. Proc.*, 45, 2739 (1986)). Utilization of calcium channel blockers may be limited by excessive vasodilation, negative inotropy, excessive depression of the sinus nodal rate, atrial-ventricular nodal conduction disturbances and interference with non-vascular smooth muscle contraction. A combination therapy which minimizes the amount of calcium channel blocker required to achieve the desired anti-hypertensive effect is desirable.

In addition to identification of essential hypertension, the existence of PHF is applicable to the study and treatment of other diseases which may or may not necessarily include hypertension as a primary symptom. These diseases include non-insulin-dependent diabetes mellitus (NIDDM) and cancer. In NIDDM, increased intracellular free calcium has been observed. The increase can be attributed to PHF. PHF has been detected in the plasma of "ob/ob" mice which are obese, hypertensive and have non-insulin-dependent diabetes. PHF is also found in humans with essential hypertension, e.g., hypertension of the low-renin and salt-sensitive type, and in a higher percentage of humans with NIDDM than those without NIDDM [see Ho et al., *Journal of Cardiovasc. Pharmacol.*, 23 (Supp. 2): S31–S34 (1994)].

Some forms of cancer are characterized by an increase in intracellular free calcium [see: Okazaki et al., *Canc. Res.*, 46 (12 Pt 1), 6059–6063 (1986); Lipton and Morris, *Canc. Chemother. Pharmacol.*, 18(1), 17–20 (1986); Chien and Warren, *Canc. Res.*, 46(11), 5706–5714; Shirakawa et al., *Canc. Res.*, 46(2), 658–661 (1986); and Meyer, *J. Hypertens.*, 5 (suppl. 4), S3–S4 (1987)]. As PHF is of parathyroid origin, PHF may be implicated in those forms of cancer characterized by an increase in intracellular calcium concentration.

BRIEF SUMMARY OF THE INVENTION

It now has been discovered that the use of supplemental dietary calcium and calcium channel blockers in combination is an effective method of treatment for disease associated with excessive PHF. Such diseases include, but are not limited to, hypertension, atherosclerosis, congestive heart failure, NIDDM and some forms of cancer which are characterized by an increase in intracellular calcium concentration, such as breast cancer and colon cancer. The combination therapy employing both agents is more effective and predictable than the use of either agent alone. The effect is greater than the sum of the effects of both agents separately, or synergistic, with respect to dihydropyridines. One does not observe the synergistic effects with the benzeneacetonitriles; however, the present inventors have found that the combination therapy with benzeneacetonitriles and calcium gives a higher predictability of a dose response. That is, with a benzeneacetonitrile as the calcium channel blocker, a dose response relation is more apparent and there is smaller standard error, as compared to the other classes of calcium channel blockers (e.g., dihydropyridines).

DETAILED DESCRIPTION OF THE INVENTION

We have discovered that a significant number of hypertensive mammals, including 30–40% of human hypertensives [Resnick et al., *J. Hypertens.*, 11:1235–1241 (1993)], have measurable levels of a parathyroid-derived hormone which increases the uptake of calcium ions in vascular tissues. We have also discovered that a significant number of patients with atherosclerosis, congestive heart failure, NIDDM and some forms of cancer have detectable activity of the same factor. This factor, which we have named parathyroid hypertensive factor, or PHF, has been isolated from spontaneously hypertensive rats (SHR) and a similar substance has been identified in human hypertensives, patients with atherosclerosis, congestive heart failure, NIDDM and breast and colon cancer patients. Application Ser. No. 07/327,450, which is incorporated herein by reference, describes the characteristics of PHF and discloses methods for its identification.

The procedure for detecting the presence of PHF activity is a blood pressure bioassay. A patient's plasma sample is obtained in a heparinized tube, centrifuged and dialyzed at a 1000 molecular weight cut-off. The dialyzed plasma sample is injected into SD rats at a dose of 4.0 ml/kg. Rat mean arterial pressure (MAP) is recorded and PHF activity is quantified as the peak of the prolonged increase in blood pressure occurring 40–60 minutes after injection.

Table 1 shows that a higher percentage of humans with NIDDM have detectable PHF activity in their blood.

TABLE 1

Direction of change in rat blood pressure during bioassay to measure parathyroid hypertensive factor activity in human plasma

| | Increased | | Unchanged | | Decreased | |
|---|---|---|---|---|---|---|
| | % | (n) | % | (n) | % | (n) |
| Diabetic | 65.4 | (121) | 9.7 | (18) | 24.9 | (46) |
| Non-diabetic | 33.1 | (42) | 26.8 | (34) | 40.2 | (51) |

Table 2 shows that colon cancer and breast cancer patients experience a significant positive PHF response.

TABLE 2

PHF activity in plasma samples taken from cancer patients

| | # of Patients | # of Patients Positive for PHF | mean PHF response (mmHg) |
|---|---|---|---|
| Colon Cancer | 11 | 7 | 11.6 |
| Breast Cancer | 28 | 15 | 8.3 |

Figure 1:
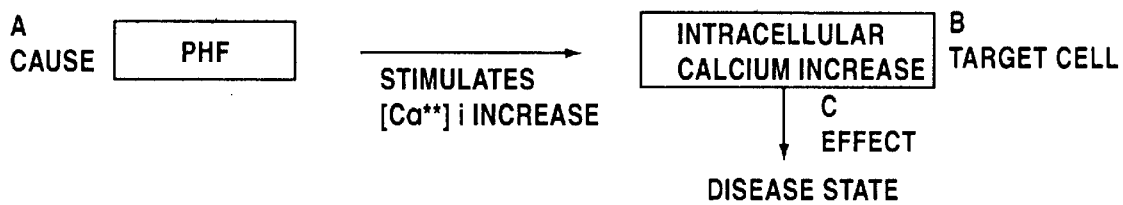
FIG. 1 illustrates the method of stimulating a target cell by PHF which increases calcium uptake.
Figure 2:
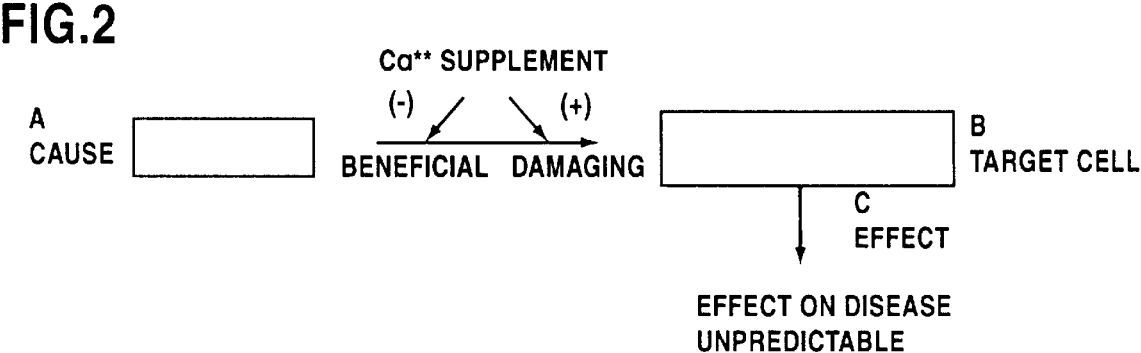
FIG. 2 illustrates the beneficial and damaging effects of calcium supplementation alone.
Figure 3:
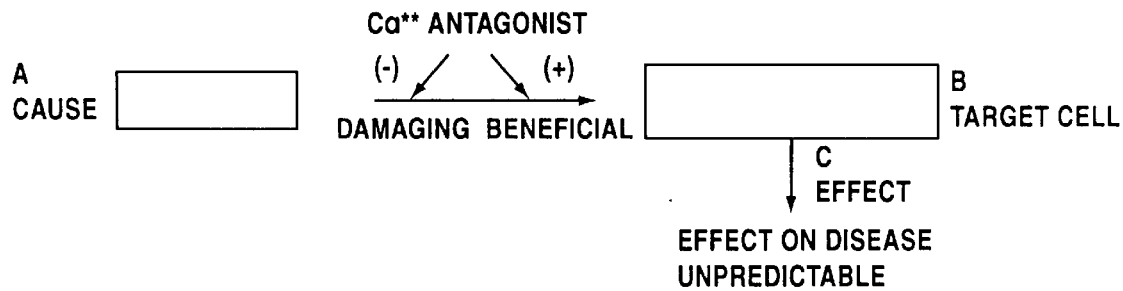
FIG. 3 illustrates the beneficial and damaging effects of calcium antagonists.
Figure 4:
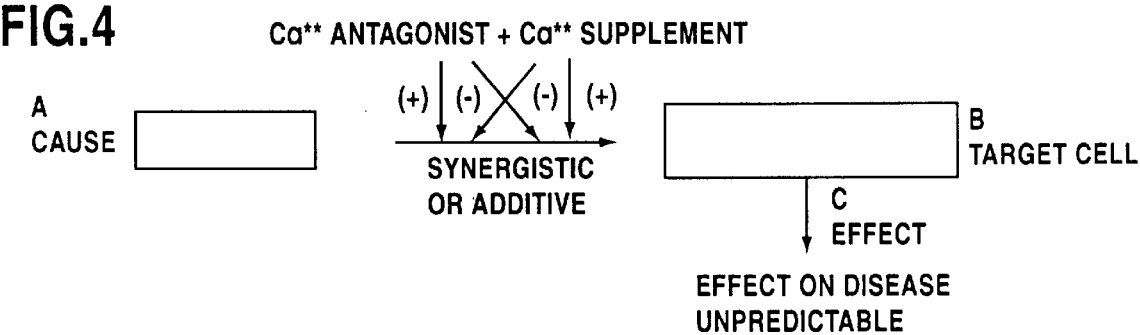
FIG. 4 illustrates the advantages of combination therapy, either additive or synergistic, in improving the magnitude and predictability of response.
Figure 5:
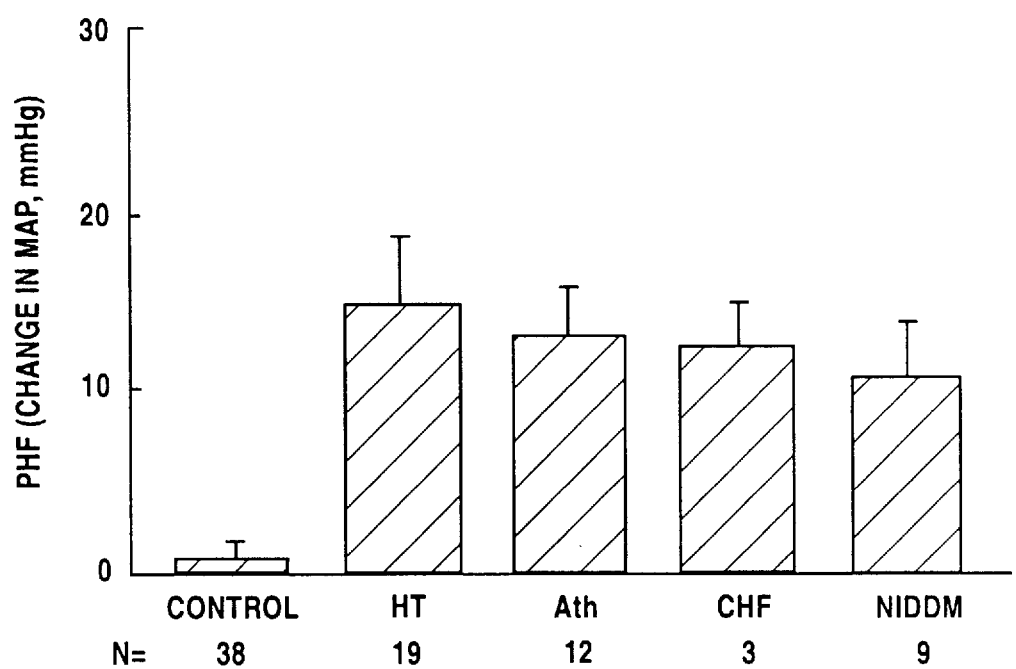
FIG. 5 illustrates the presence of PHF in patients with hypertension (HT), atherosclerosis (Ath), congestive heart failure (CHF), and non-insulin dependent diabetes mellitus (NIDDM).

FIG. 5 illustrates the presence of PHF for selected diseases in patients attending a clinic. PHF was detected using a blood pressure bioassay, thus the unit of measure is mean arterial pressure (MAP) in mm Hg. FIG. 5 illustrates the presence of PHF in patients with hypertension (HT), atherosclerosis (Ath), congestive heart failure (CHF), and non-insulin dependent diabetes mellitus (NIDDM).

It has been found that the production of PHF, as well as renin, can be inhibited by supplemental calcium and that increased levels of supplemental calcium are effective in reducing hypertension. However, the effects of calcium supplementation alone are unpredictable due to the fact that high levels of calcium in the blood may increase the bioavailability of calcium to vascular smooth muscle tissue, limiting the anti-hypertensive effect. In addition, very high levels of dietary calcium may result in undesirable and painful calcium deposits in joints and may lead to kidney stones.

The use of combination therapy involving both calcium channel blockers and dietary calcium supplementation is believed to affect both the consequences of PHF activity and PHF itself. The calcium channel blocker is believed to block the pharmacological action of PHF through blocking calcium channels, while the calcium supplement is believed to block the release of PHF into the circulation.

The use of combination therapy involving both calcium channel blockers and dietary calcium supplementation allows the requisite lowering of blood pressure in hypertensives as well as treatment of other PHF-related diseases, including atherosclerosis, congestive heart failure, NIDDM and some forms of cancer characterized by an increase in intracellular calcium concentration, such as breast cancer and colon cancer, using smaller doses of the channel blocker while obtaining a greater treatment effect. Other diseases exist which display abnormal intracellular calcium regulation. It is expected that these diseases also involve excessive PHF, and therefore, based on the results regarding other PHF-related diseases, would be treatable using combination therapy. Such diseases include obesity, immune disturbances, cystic fibrosis, aging, dementias such as Alzheimer's disease, asthma, chronic obstructive pulmonary disease, cataracts, peptic ulcer disease, inflammatory bowel disease, hyperlipidemia, endocrine hyperplasias, shock and other forms of cancer characterized by an increase in intracellular calcium concentration, such as kidney cancer, T-cell leukemia and prostate cancer.

Combination therapy is particularly suitable for long-term therapy to avoid the untoward side effects of excessive use of either calcium or a calcium channel blocker individually. By "calcium channel blockers" is meant any pharmaceutical composition which inhibits the entry of calcium or inhibits the mobilization of calcium from intracellular stores. Representative examples of useful calcium channel blockers are dihydropyridines such as nifedipine, benzothiazepenes such as diltiazem, and benzeneacetonitriles such as verapamil. As a result, not only is the therapy improved and side effects reduced, but the cost of treatment may be dramatically lowered, because the cost of calcium supplementation is much lower than the cost of available calcium channel blockers.

An effective alternative to the administration of calcium supplements, particularly when the diet contains adequate calcium, is to administer an effective form of Vitamin D, such as $1\alpha, 25\text{-}(OH)_2D_3$ to increase calcium uptake in the duodenal mucosa.

When calcium and/or $1\alpha, 25\text{-}(OH)_2D_3$ is administered in combination with a calcium channel blocker, the active components may be combined in a single capsule containing appropriate unit doses of each. Patient compliance is improved when only one "medicine" is required.

The active components of the invention may also be included in a kit which is comprised of separate containers, each containing an individual dose of a therapeutically effective amount of a calcium compound and/or an effective form of Vitamin D, such as $1\alpha, 25\text{-}(OH)_2D_3$, and a calcium channel blocker. The kit may also contain use instructions in the form of a package insert.

The use of combination therapy involving a calcium channel blocker and calcium and/or an effective form of Vitamin D such as $1\alpha, 25\text{-}(OH)_2D_3$ reduces the daily dosage of channel blocker required to less than half the dosage usually required, sometimes to as little as one-fifth of the dosage required for the channel blocker alone.

A particular advantage of the combination of a calcium channel blocker and either or both of calcium and 1α, 25-(OH)$_2$D$_3$ is the predictability of the therapy. The dose-response curve for nifedipine is not predictable in an individual patient, and a considerable period of time may be necessary to ascertain the appropriate dosage. The effect of exogenous calcium supplementation is not predictable, depending on numerous factors including rate of uptake, rate of excretion, parathyroid hormone levels and PHF levels. Somewhat surprisingly, therefore, it has been found that the combination of a calcium channel blocker and calcium supplement is not only synergistic, but that the dose response is more predictable. The predictability is especially apparent with benzeneacetonitriles. The dose response curve is more linear and there is a smaller standard error when the calcium channel blocker is of the benzeneacetonitrile class. The time period over which a patient must be titrated is shortened and the potential for side effects is reduced because the therapeutic index is effectively raised.

The dosage of a combination pharmaceutical preparation which is used depends upon the needs of the individual patient. Typical formulations would be in capsule, tablet, powder or granular forms containing ⅕ to ½ of the conventional dosage of a calcium channel blocker, preferably 5 mg of nifedipine, with 500 mg of calcium carbonate and/or ca. 10–25 USP units (0.05 μg) of 1α, 25-(OH)$_2$D$_3$. The calcium supplement should be present in an amount whereby the ratio by weight of elemental calcium to dihydropyridine is at least 40:1. With respect to verapamil, formulations would contain a molar ratio of elemental calcium to verapamil of 5:1 to 500:1, preferably 10:1 to 250:1. The formulations may also contain pharmaceutically acceptable carriers and stabilizers as appropriate.

The formulations using the active components of the invention have been shown to be useful in treating hypertension, which is associated with excessive PHF; thus, a similar dose may be used in treating other PHF-related diseases, including, but not limited to, atherosclerosis, congestive heart failure, NIDDM and some forms of cancer characterized by an increase in intracellular calcium concentration, such as breast cancer and colon cancer.

The combination of a calcium channel blocker and a calcium supplement is effective in treating hypertension, and is compatible with other pharmaceutical compounds used for control of hypertension and angina such as angiotensin converting enzyme (ACE) inhibitors, β-adrenergic antagonists, nitrates, and diuretics. The combination therapy of calcium with a benzeneacetonitrile (e.g., verapamil) is not synergistic but is statistically additive, the data suggesting that a lowering of blood pressure is more predictable.

The invention is illustrated by the following examples, which are not limitative of the invention. Modification, such as would be understood by those skilled in the art, is within the scope of applicants' invention. In the case of treating hypertension, such modifications include the additional use of α- and β-adrenergic blocking pharmaceuticals, diuretics, and other agents suitable for treatment of hypertension and angina by other mechanistic pathways.

EXAMPLE 1

A patient with diabetes is given a dosage of 5 mg of nifedipine and 200 mg of elemental calcium in the form of calcium carbonate. The result is a reduction in the insulin/oral hypoglycemic requirement in the diabetic patient.

EXAMPLE 2

A patient with breast cancer is given a dosage of 30 mg of verapamil and 300 mg of elemental calcium in the form of calcium carbonate. The result is a reduction in tumor growth rate in the breast cancer patient.

EXAMPLE 3

A patient with colon cancer is given a dosage of 5 mg of verapamil and 1250 mg of elemental calcium in the form of calcium carbonate. The result is a regression in tumor size in the colon cancer patient.

We claim:

1. A method of treating non-insulin dependent diabetes mellitus in a patient in need thereof, comprising coadministering to the patient
   (a) a dihydropyridine calcium channel blocking agent; and
   (b) a calcium supplement,
      wherein the ratio by weight of elemental calcium to dihydropyridine calcium channel blocking agent is at least 40:1, and the dihydropyridine calcium channel blocking agent and the calcium supplement are present in respective amounts whereby, in combination, they are synergistically effective in treating the non-insulin dependent diabetes mellitus in the patient.

2. The method of claim 1, wherein the dihydropyridine calcium channel blocking agent is nifedipine.

3. The method of claim 1, wherein the calcium supplement is calcium carbonate.

* * * * *